US012766333B2

(12) United States Patent
Ning et al.

(10) Patent No.: US 12,766,333 B2
(45) Date of Patent: Oct. 20, 2026

(54) SYSTEMS AND METHODS FOR INTEGRATED ELECTRIC FIELD SIMULATION AND NEURONAVIGATION FOR TRANSCRANIAL MAGNETIC STIMULATION

(71) Applicant: The General Hospital Corporation, Boston, MA (US)

(72) Inventors: Lipeng Ning, Boston, MA (US); Joan A. Camprodon, Charlestown, MA (US); Yogesh Rathi, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 993 days.

(21) Appl. No.: 17/996,725

(22) PCT Filed: Apr. 22, 2021

(86) PCT No.: PCT/US2021/028644
§ 371 (c)(1),
(2) Date: Oct. 20, 2022

(87) PCT Pub. No.: WO2021/216874
PCT Pub. Date: Oct. 28, 2021

(65) Prior Publication Data

US 2023/0211168 A1 Jul. 6, 2023

Related U.S. Application Data

(60) Provisional application No. 63/013,749, filed on Apr. 22, 2020.

(51) Int. Cl.
*A61N 2/02* (2006.01)
*A61N 2/00* (2006.01)

(52) U.S. Cl.
CPC ............... *A61N 2/006* (2013.01); *A61N 2/02* (2013.01)

(58) Field of Classification Search
CPC .................................................. A61N 2/00-12
See application file for complete search history.

(56) References Cited

U.S. PATENT DOCUMENTS 7,239,910 B2 7/2007 Tanner
7,711,431 B2 5/2010 Tanner et al.
(Continued)

FOREIGN PATENT DOCUMENTS

WO 2012164172 A1 12/2012
WO 2019050225 A1 3/2019
(Continued)

OTHER PUBLICATIONS

Saturnino et al., "SimNIBS 2.1: A Comprehensive Pipeline for Individualized Electric Field Modelling for Transcranial Brain Stimulation," in: Makarov, S., Horner, M., Noetscher, G. (eds) Brain and Human Body Modeling. Springer, Cham. https://doi.org/10.1007/978-3-030-21293-3_1 (Year: 2019).*
(Continued)

*Primary Examiner* — Thaddeus B Cox
(74) *Attorney, Agent, or Firm* — QUARLES & BRADY LLP

(57) ABSTRACT

A system for integrated electric field simulation and neuronavigation includes a neuronavigation system configured to track an electromagnetic coil used for neuromodulation of a brain of a subject and an electric field simulation neural network coupled to the neuronavigation system. The electric field simulation neural network is configured to generate a simulated electric field for a region of interest based at least on a coil position and orientation, a magnetic field profile of the electromagnetic coil, and multimodal neuroimaging data
(Continued)

associated with the subject. The system further includes a display coupled to the electric field simulation neural network and configured to display the simulated electric field. The region of interest can be the brain of the subject and the electromagnetic coil can be a transcranial magnetic stimulation (TMS) coil.

21 Claims, 8 Drawing Sheets

(56) References Cited

U.S. PATENT DOCUMENTS

| | | | |
|---|---|---|---|
| 10,070,802 B2 | 9/2018 | Paitel et al. | |
| 10,292,645 B2 | 5/2019 | Saitoh et al. | |
| 2004/0138550 A1 | 7/2004 | Hartlep et al. | |
| 2017/0049387 A1* | 2/2017 | Saitoh | G16H 30/40 |
| 2017/0087367 A1* | 3/2017 | Weisend | A61N 1/0476 |
| 2018/0104500 A1 | 4/2018 | Blum et al. | |
| 2019/0126055 A1 | 5/2019 | Etkin et al. | |
| 2019/0336018 A1 | 11/2019 | Williams et al. | |
| 2020/0214570 A1 | 7/2020 | Kim | |

FOREIGN PATENT DOCUMENTS

| | | |
|---|---|---|
| WO | 2019050226 A1 | 3/2019 |
| WO | 2019212804 A1 | 11/2019 |

OTHER PUBLICATIONS

Yokota, T. et al., Real-Time Estimation of Electric Fields Induced by Transcranial Magnetic Stimulation with Deep Neural Networks, Brain Stimulation, 2019, 12:1500-1507.

PCT International Search Report and Written Opinion, PCT/US2021/028644, Aug. 11, 2021, 11 pages.

European Patent Office, Extended Search Report, Application No. 21791717.8, Mar. 20, 2024, 9 pages.

* cited by examiner

SYSTEMS AND METHODS FOR INTEGRATED ELECTRIC FIELD SIMULATION AND NEURONAVIGATION FOR TRANSCRANIAL MAGNETIC STIMULATION

CROSS-REFERENCE TO RELATED APPLICATIONS

This application represents the U.S. national stage entry of International Application No. PCT/US2021/028644 filed Apr. 22, 2021, which is based on and claims priority to U.S. Ser. No. 63/013,749 filed Apr. 22, 2020, and entitled "System and Method for Simultaneous Electric Field Stimulation and Neuronavigation for Transcranial Magnetic Stimulation." The contents of these applications are incorporated herein by reference in their entirety.

STATEMENT REGARDING FEDERALLY SPONSORED RESEARCH

This invention was made with government support under MH115280 awarded by the National Institutes of Health. The government has certain rights in the invention.

FIELD

The present disclosure relates generally to neuromodulator systems and, more particularly, to systems and methods for integrated electric field simulation and neuronavigation that enable real-time graphical rendering of electric fields stimulated by an electromagnetic coil and that enable optimization of coil position and orientation.

BACKGROUND

Transcranial magnetic stimulation (TMS) is a noninvasive neuromodulation technique used for basic neuroscience and clinical applications, including diagnostic (e.g., motor system biomarkers, pre-surgical mapping) and therapeutic (e.g., major depression disorder, obsessive compulsive disorder, migraines). TMS uses magnetic fields to stimulate nerve cells in the brain of the subject. The magnetic fields are generated by an electromagnetic coil that is placed over the scalp of the subject to induce electric currents in the underlying brain tissue. The magnetic fields are generated by electric pulses applied to and flowing though the electromagnetic coil. The magnetic fields pass through the skull and into the brain. The position of the coil over the scalp of the subject is selected to focus on and target a specific area or site of the brain for stimulation. The target region of the brain is usually determined by the structure or function of the brain estimated using neuroimaging techniques such as functional magnetic resonance imaging (fMRI). The brain target is typically selected on the surface of the brain, which is not visible in the real space. The goal of TMS is to generate sufficiently strong magnetic fields in a specific region of the brain of the patient to stimulate the appropriate brain network based on the diagnostic or therapeutic application. It is desirable to place the TMS coil in a position selected so that, for example, the target region in the brain has the strongest possible electric field.

The definition and selection of the coil position on the surface of the skull to optimally engage the desired brain target is critical for all applications, but certainly essential for diagnostic and therapeutic clinical uses. In addition, accurate localization of a brain target is critical to reaching optimal treatment response in TMS. Typically, the coil may be positioned over the head based on external landmarks and measurements. Given that TMS is noninvasive, TMS practitioners have traditionally relied on either skull fiducial markers or stereotactic neuronavigation systems that assume the point with the shortest distance from the brain target to the skull is where the coil should be located. However, these techniques do not take into account the impact of tissues between the coil and the brain on the distribution of the magnetic and induced electric fields. This can lead to inaccuracies in positioning the coil and targeting the brain area. Because of complex brain structure, the point on the scalp that is closest to the brain target may not be the optimal position. Moreover, the electric field (E-field) induced in the brain not only depends on the position of the coil but also depends on the orientation of the coil.

Neuronavigation systems and electric field simulation are techniques that are currently used in clinical settings to improve the localization of the brain target in TMS and overcome problems of positioning based on external landmarks. Currently, neuronavigation and E-field simulation tools are separately used in TMS. Neuronavigation is a computer assisted system that is used in TMS to ensure that the relative position of the coil and the head in real space matches the position in image space. Neuronavigation technology visualizes the patient's brain based on imaging data, for example, magnetic resonance imaging (Mill) data), in order to navigate and correctly position the coil to target the desired brain structure or region. In addition, neuronavigation systems may be configured to track and monitor the position of the coil (e.g., using an infrared camera in combination with the imaging data) on a reconstruction of the patient's head or brain during the duration of the TMS stimulation session. Neuronavigation systems can track the position of the TMS coil relative to a target or relative to an anatomical area of interest. Typically, software is used for E-field simulation to estimate the E-field for a specific coil position and orientation. However, current E-field simulation approaches usually take several minutes to compute the E-field for a specific coil position. If that coil position is not optimal, then a different position needs to be examined. Because of the long estimation time, only a few positions are typically examined in practice, making the selected coil position sub-optimal. In addition, current E-simulation tools are not practical in clinical setting because they are too slow to be integrated with neuronavigation systems to respond to any adjustment of coil position by clinicians in real time. Moreover, clinicians are not fully informed by neuronavigation systems about the stimulated brain site relative to different coil positions.

It would be desirable to provide a system and method that integrates electric field simulation and neuronavigation, and enables, for example, real-time graphical rendering of electric fields stimulated by an electromagnetic coil at a given position, and optimization of coil position and orientation.

SUMMARY

In accordance with an embodiment, a system for integrated electric field simulation and neuronavigation includes a neuronavigation system configured to track an electromagnetic coil used for neuromodulation of a brain of a subject and an electric field simulation neural network coupled to the neuronavigation system. The electric field simulation neural network is configured to generate a simulated electric field for a region of interest based at least on a coil position and orientation, a magnetic field profile of the electromagnetic coil, and multimodal neuroimaging data associated with the subject. The system further includes a display coupled to the electric field simulation neural network and configured to display the simulated electric field.

In accordance with another embodiment, a method for generating a graphical rendering of a simulated electric field using a system for integrated electric field simulation and neuronavigation includes detecting, using a neuronavigation system, a position and orientation of an electromagnetic coil used for neuromodulation of a brain of a subject and providing the position and orientation of the electromagnetic coil, a magnetic field profile of the electromagnetic coil and multimodal neuroimaging data associated with the subject to an electric field simulation neural network. The method further includes generating, using the electric field simulation neural network, a simulated electric field for a region of interest based at least on the position and orientation of the electromagnetic coil, the magnetic field profile of the electromagnetic coil, and the multimodal neuroimaging data associated with the subject. The method further includes generating, using a graphical rendering module, a graphical rendering of the simulated electric field, and displaying the graphical rendering on a display.

In accordance with another embodiment, a method for optimizing a position and orientation of an electromagnetic coil of a neuromodulation system using a system for integrated electric field simulation and neuronavigation includes providing a position and orientation of an electromagnetic coil, a magnetic field profile of the electromagnetic coil and multimodal neuroimaging data associated with a subject to an electric field simulation neural network. The electromagnetic coil may be used for neuromodulation of a brain of the subject. The method further includes generating, using the electric field simulation neural network, a simulated electric field for a region of interest based at least on the position and orientation of the electromagnetic coil, the magnetic field profile of the electromagnetic coil, and the multimodal neuroimaging data associated with the subject. The method further includes receiving a reference target in the region of interest, comparing, using an optimization module, the simulated electric field to the reference target to determine if the position and orientation of the electromagnetic coil maximizes an electric field at the reference target in the region of interest, and providing the position and orientation of the electromagnetic coil to a neuronavigation system if the position and orientation of the electromagnetic coil maximizes an electric field at the reference target in the region of interest.

BRIEF DESCRIPTION OF THE DRAWINGS

The present disclosure will hereafter be described with reference to the accompanying drawings, wherein like reference numerals denote like elements.

DETAILED DESCRIPTION

The present disclosure describes systems and methods for integrating electric field (E-field) simulation with neuronavigation to improve targeting of brain regions (including selection of coil position) for neuromodulation techniques such as, for example, transcranial magnetic stimulation (TMS). In some embodiments, the integrated E-field simulation and neuronavigation system may be used to generate a graphical rendering of electric fields for a coil position which, for example, enables the visualization of the electric field in the brain in real time after adjusting the coil position. In some embodiments, the integrated E-field simulation and neuronavigation system may be used to optimize the coil position and orientation and enable the selection of an optimal coil position. The optimization of the coil position and orientation can be, for example, critical for treatment planning for a neuromodulation technique such as TMS and can improve the accuracy of diagnostic applications. Advantageously, the E-field simulation may be performed using a machine learning neural network that allows for ultra-fast computation and rendering of E-fields that will be generated when the brain is stimulated using an electromagnetic coil (e.g., a TMS coil). In addition, the disclosed systems and methods for integrating E-field simulation and neuronavigation can also advantageously be used to automatically optimize the coil position to match the electric field with the expected brain target to improve the precision of the brain stimulation.

Figure 1:
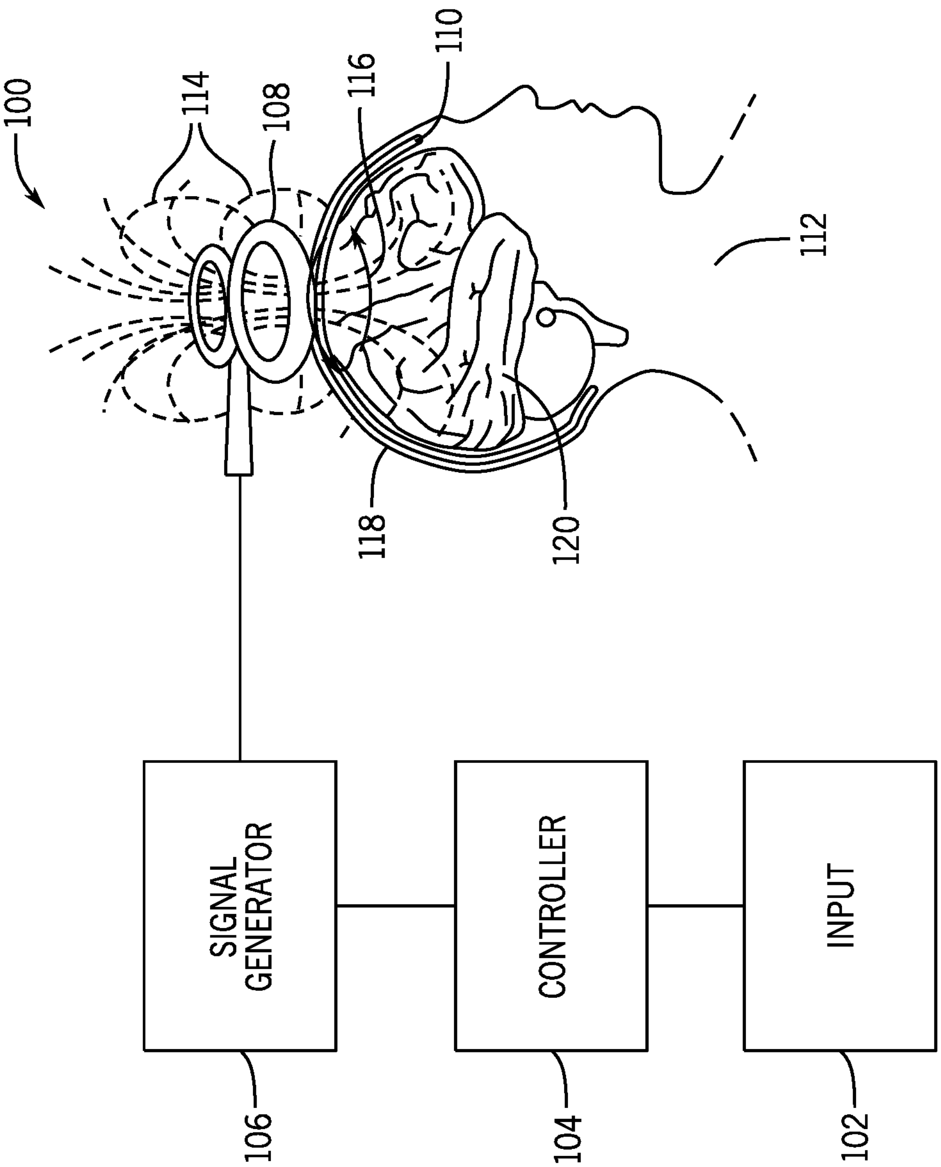
FIG. 1 is a block diagram of an example transcranial magnetic stimulation (TMS) system in accordance with an embodiment.

FIG. 1 is a block diagram of an example transcranial magnetic stimulation (TMS) system in accordance with an embodiment. A TMS system 100 may include an input 102, a controller 104, a signal generator 106 and an electromagnetic coil 108. The controller 104 is in communication with the signal generator 106 and is configured to direct the signal generator 106 to provide various signals to the coil 108. In some implementations, the controller 104 may be any general-purpose computing system or device, such as a personal computer, workstation, cellular phone, smartphone, laptop, tablet, or the like. As such, the controller 104 may include any suitable hardware and components designed or capable of carrying out a variety of processing and control tasks, including steps for optimizing and directing the signal generator 106 to provide various signals to the coil 108. For example, the controller 104 may include a programmable processor or combination of programmable processors, such as central processing units (CPUs), graphics processing units (GPUs), and the like. In some implementations, the controller 104 may be configured to execute instructions stored in a non-transitory computer readable-media. In this regard, the controller 104 may be any device or system designed to integrate a variety of software, hardware, capabilities and functionalities. Alternatively, and by way of particular configurations and programming, the controller

104 may be a special-purpose system or device. For instance, such special-purpose system or device may include one or more dedicated processing units or modules that may be configured (e.g., hardwired, or pre-programmed) to carry out steps, in accordance with aspects of the present disclosure.

The electromagnetic coil 108 is positioned proximate to and over the head, for example, the scalp 118, of a subject 112. The electromagnetic coil 108 may be insulated using known methods and materials. In some embodiments, the coil 108 may be positioned and held in place over the scalp 118 by an operator or using a mechanical arm (not shown). The position of the coil 108 over the scalp 118 is selected to target and stimulate a specific area of the brain (e.g., a region, site or target in the brain). Accordingly, the coil 108 may be positioned over the region to be stimulated in the brain. Signal generator 106 is configured to generate and deliver electrical signals (e.g., electric current or voltage signals) to the coil 108. The electric current delivered from the signal generator 106 and flowing through the coil 108 generates a magnetic field 114. The magnetic field 114 (e.g., magnetic pulses) passes through the skull 110 and into the brain 120 of the subject 112 and cause or induce electrical currents 116 that stimulate nerve cells in the targeted brain region. Different coil types may be used for coil 108 to elicit different magnetic field patterns. The strength and distribution of the time-varying magnetic fields 114 may be dependent on both the geometry and the amount of current traveling through the coil 108. The induced electric field 114 may also be dependent on fixed variables unique to individual subjects such as the geometry and electrical properties of anatomies in and around the brain.

In some embodiments, the signals generated by the signal generator 106 and provided to the coil 108 may be in the form of a pulse sequence having a plurality of pulses. The power, amplitude, duration, shape, and frequency of the pulses may be selected to achieve a desired level of or depth of stimulation, as well as to optimize heat or magnetic forces induced in the coil 108. An operator may select the specific type and characteristics of the electric pulses to be generated by the signal generator 106 using an input 102 coupled to the controller 104. The input 103 can be, for example, a keyboard, a mouse, a touch screen, etc. While the following description will be discussed in referenced to a TMS system and a TMS coil, it should be understood that the systems and methods described herein may be used with other types of noninvasive neuromodulation systems.

Figure 2:
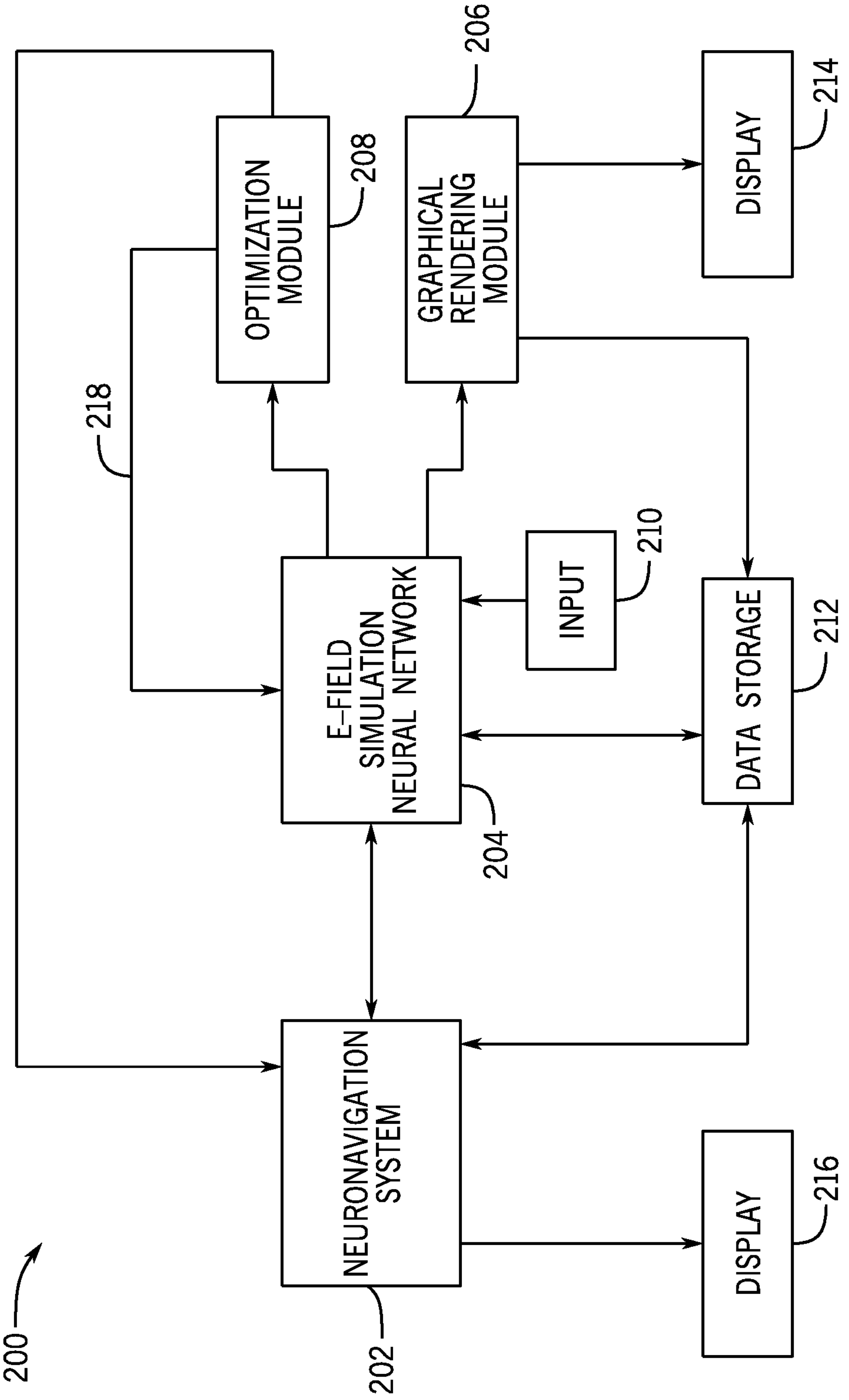
FIG. 2 is a block diagram of a system for integrated electric field simulation and neuronavigation in accordance with an embodiment.

FIG. 2 is a block diagram of a system for integrated electric field simulation and neuronavigation in accordance with an embodiment. The system 200 includes a neuronavigation system 202, an electric field (E-field) simulation neural network 204, a graphical rendering module 206 and an optimization module 208. Neuronavigation system 202 is configured to, for example, visualize a subject's brain based on imaging data, for example, magnetic resonance imaging (MRI) data), and to track and monitor the position of a coil (e.g., a TMS coil) on the visualization of the subject's head or brain. In some embodiments, the neuronavigation system 202 can track the position of the TMS coil relative to a target or relative to an anatomical area of interest. The neuronavigation system 202 may be any known neuronavigation system in the art. Neuronavigation system 202 may be coupled to a display 216 to display images of a subject's head and brain, tracking of a coil used for TMS, and other information associated with the subject being treated with TMS. The neuronavigation system 202 may also be coupled to data storage 212 from which it may retrieve data or may provide information to for storage. The neuronavigation system 202 is coupled to and in signal communication with the E-field simulation neural network 204. The neuronavigation system 202 and the E-field simulation neural network 204 may be configured to exchange data such as, for example, the neuronavigation system 202 may provide a current coil position and orientation to the E-field simulation neural network 204 for analysis as discussed further below with respect to FIGS. 4 and 5, and the E-field simulation neural network 204 may provide an E-field simulation (or estimation) or an optimized coil position and orientation to the neuronavigation system 202 as discussed further below with respect to FIGS. 6-7. The E-field simulation neural network 204 is configured to generate an estimation or simulation of the E-fields that may be generated by stimulation of a subject's brain using a TMS coil. As discussed further below, the E-field simulation neural network 204 may be configured to generate an E-field simulation based on a plurality of inputs 210 including, but not limited to, a position and orientation of a TMS coil, a magnetic field profile of the TMS coil, and multimodal neuroimaging data associated with a subject being treated with a TMS system. The input 210 may be provided by an operator (e.g., by using an input such as a keyboard, a mouse, a touch screen, etc. or may be retrieved from data storage (or memory) 212.

The E-field simulation neural network 204 is coupled to a graphical rendering module 206 and an optimization module 208. In an embodiment, the neuronavigation system 202 provides a current position and orientation of a TMS coil to the E-field simulation neural network 204 which estimates the E-fields for the current position and orientation. The simulated E-fields can then be provided to and used by the graphical rendering module 206 to generate a graphical rendering of the estimated electric fields. Known methods may be used to generate the graphical rendering of the simulated E-fields. In an embodiment, the E-field simulation neural network 204 and the graphical rendering module 206 may be implemented on a graphics processing unit (GPU) (e.g., GPU 808 shown in FIG. 8) of a computer system. As discussed below with respect to FIGS. 4 and 5, the integrated E-field simulation and neuronavigation system 200 can enable the visualization of the electric field in the brain in real time after adjusting the coil position. Graphical rendering module 206 may also be coupled to a display 214 which may be used to display the graphical rendering. In some embodiments, the display 214 and the display 216 may be separate displays or may be the same display. In another embodiment, the E-field simulation neural network 204, the optimization module 208, and a feedback loop 218 may be used to determine an optimized coil position and orientation as discussed further below with respect to FIGS. 6 and 7. The optimized coil position and orientation may be provided to the neuronavigation system 202 for tracking and navigation.

Figure 3:
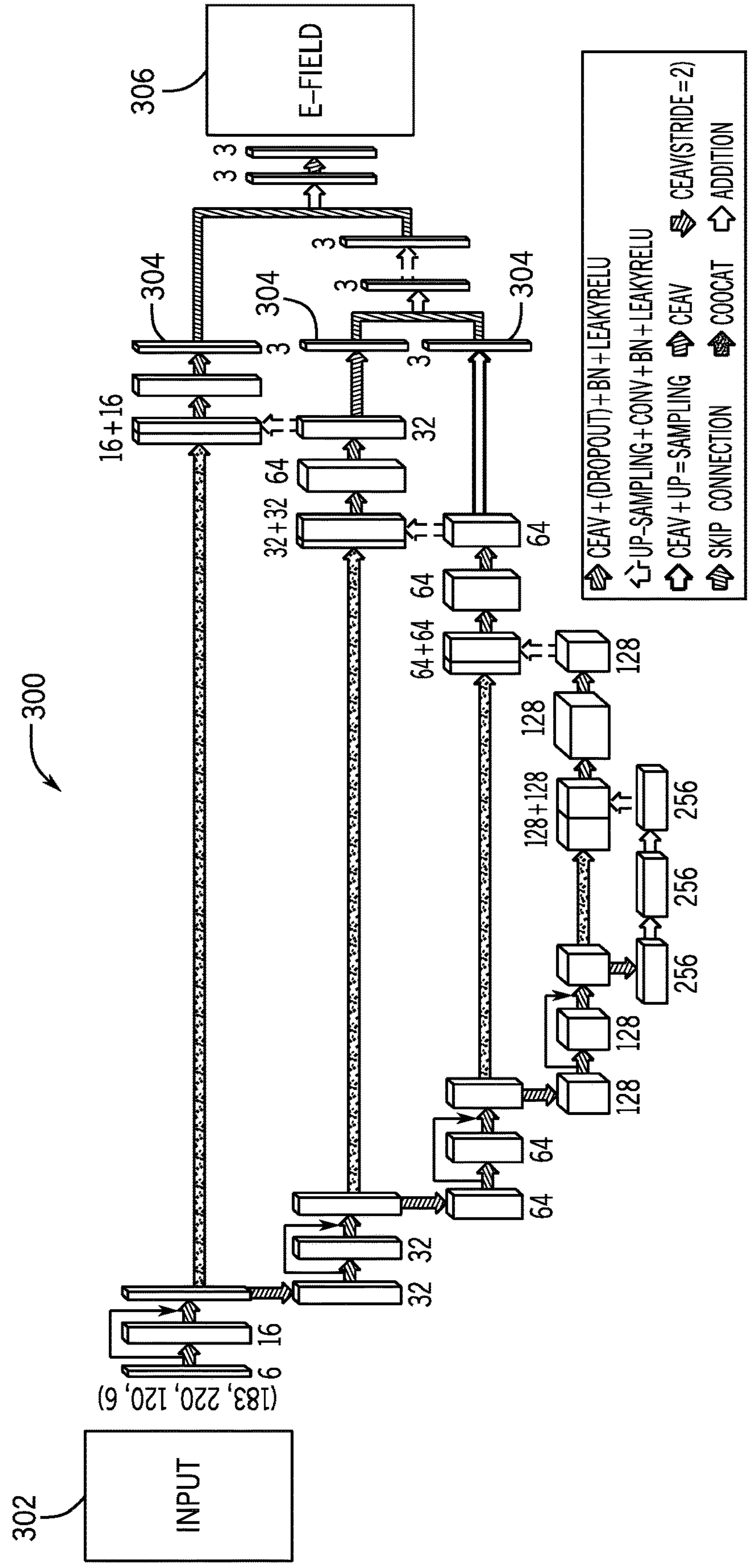
FIG. 3 illustrates an example network topology for an electric field simulation neural network in accordance with an embodiment.

Conventional E-field simulation approaches are typically too slow for a clinical setting and are limited to determining the E-field for a specific brain region. Advantageously, in the present disclosure, the E-field simulation may be performed using a neural network 204 that allows for ultra-fast computation and rendering of E-fields that may be generated when the brain is stimulated using an electromagnetic coil (e.g., a TMS coil). In addition, the E-field simulation neural network 204 can be configured to generate a global electric field simulation for a neuromodulation technique such as TMS. Accordingly, the E-field simulation neural network 204 may be configured to estimate or predict the E-field for the whole-brain of a subject for any coil position and orientation. For example, in some embodiments, the E-field simulation neural network 204 may be configured to simulate a whole-brain E-field within less than one second for a particular coil position and orientation. In some embodiments, the E-field simulation neural network generates an estimated E-field for a selected region of the brain of the subject. In some embodiments, the E-field simulation neural network 204 may generate an estimation of the E-fields for a coil orientation and position based on inputs including a magnetic field profile for the type of electromagnetic coil being used in the TMS system and multimodal neuroimaging data associated with the subject. Magnetic field profiles can be different for different types of TMS coils. The multimodal neuroimaging data may include, for example, anisotropic conductivity of the brain tissue of the subject and tissue segmentation obtained using anatomical MRI. Anisotropic conductivity of brain tissue may be determined using, for example, diffusion magnetic resonance imaging (MRI). The E-field simulation neural network 204 may be trained using known methods for training a machine learning system or model. FIG. 3 illustrates an example network topology for an electric field simulation neural network in accordance with an embodiment. The example network topology 300 shown in FIG. 3 is based on a standard ResUNet network topology. Network topology 300 may be generalized by adding a multi-scale imaging feature, represented by nodes 304, to predict an E-field 306. As mentioned, inputs 302 to the network 300 can include a magnetic field profile for the type of electromagnetic coil being used in the TMS system and multimodal neuroimaging data associated with the subject (e.g., anisotropic conductivity of the brain tissue of the subject and tissue segmentation obtained using anatomical MRI). The network 300 is a fully convolutional network that integrates long and short skip connections, i.e., the residual modules, with the encoder-decoder based UNet architecture and combines multi-scale feature maps to enhance the predication accuracy. It should be understood that in some embodiments other network topologies may be used to implement the E-field simulation neural network 204 shown in FIG. 2.

Figure 4:
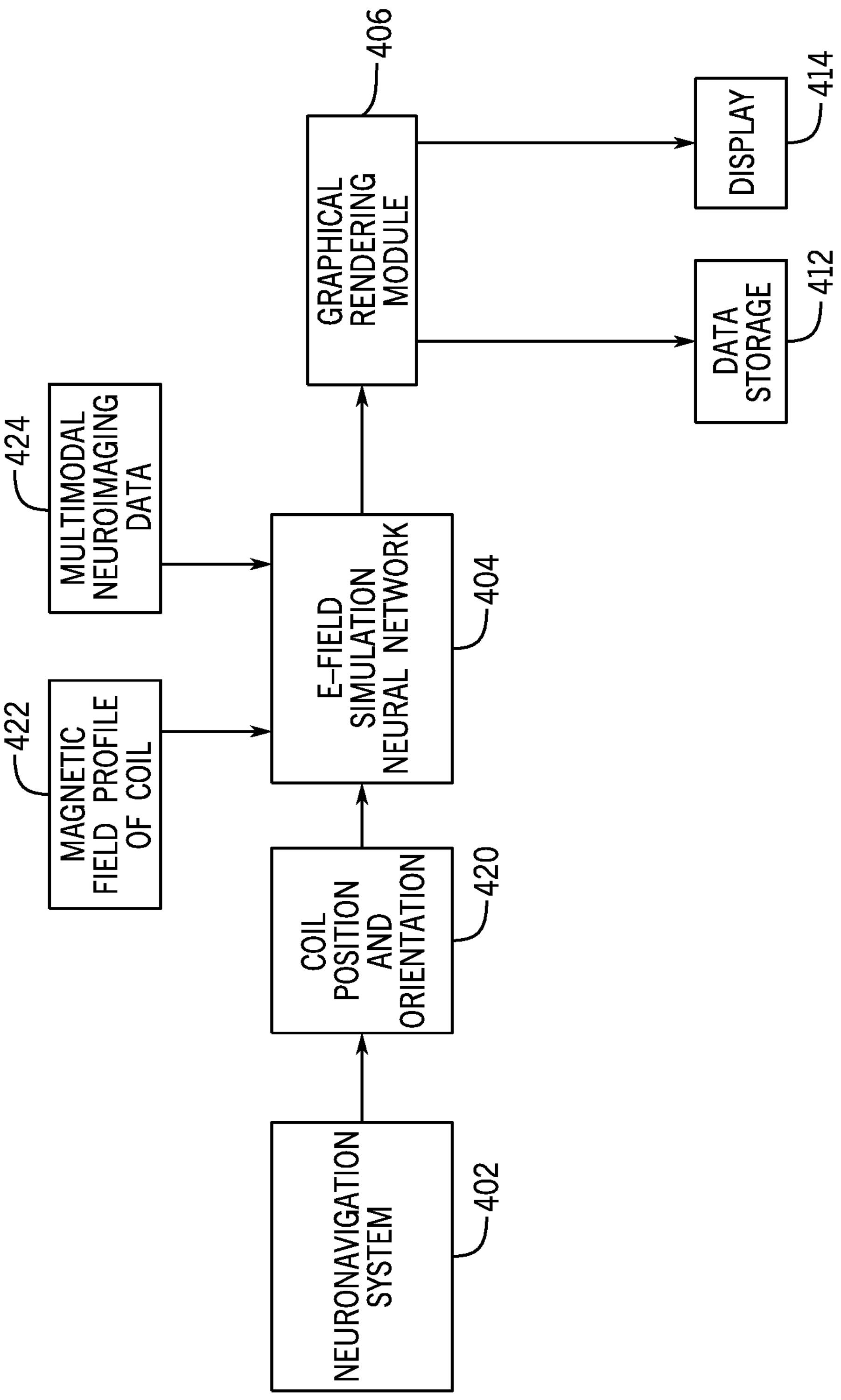
FIG. 4 is a block diagram of a workflow of the system of FIG. 2 for generating a graphical rendering of an electric field simulation in real-time in accordance with an embodiment.
Figure 5:
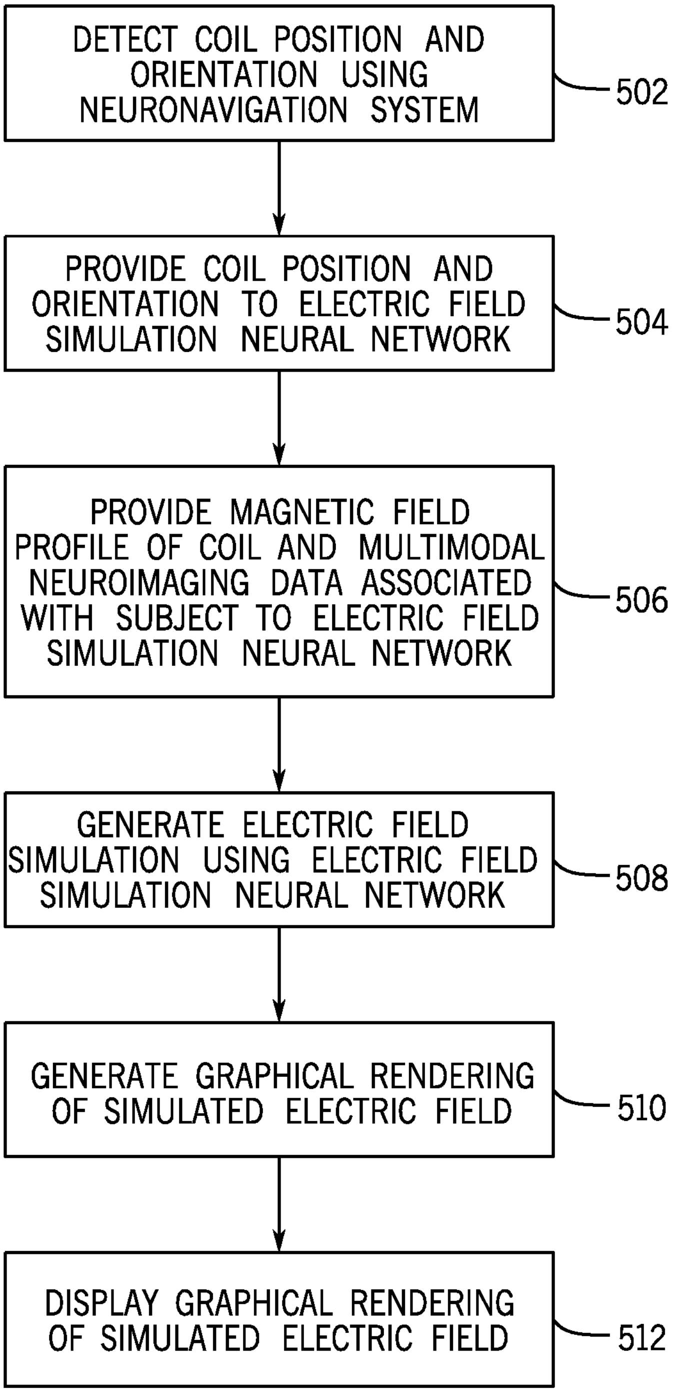
FIG. 5 illustrates a method for generating a graphical rendering of an electric field simulation in accordance with an embodiment.

As mentioned above, the system for integrated electric field simulation and neuronavigation 200 (shown in FIG. 2) may be configured to generate graphical renderings of simulated electric fields in a region of interest in real time. FIG. 4 is a block diagram of a workflow of the system of FIG. 2 for generating a graphical rendering of an electric field simulation in real-time in accordance with an embodiment and FIG. 5 illustrates a method for generating a graphical rendering of an electric field simulation in accordance with an embodiment. Referring to FIGS. 4 and 5, at block 502, a neuronavigation system 402 may be used to detect a coil position and orientation 420 for a TMS coil (e.g., coil 108 shown in FIG. 1). At bock 504, the coil position and orientation 420 may be provided to an E-field simulation neural network 404. At block 506, a magnetic field profile 422 of the TMS coil and multimodal neuroimaging data 424 associated with the subject are also provided as inputs to the E-field simulation neural network 404. In an embodiment, the magnetic field profile 422 of the coil and the multimodal neuroimaging data 424 associated with the subject may be retrieved from data storage (or memory) of, for example, the E-field simulation and neuronavigation system (e.g., data storage 212 shown in FIG. 2) or other computer system. Multimodal neuroimaging data 424 may be, for example, neuroimaging data of a subject's head and brain (e.g., functional and structural information) acquired using a plurality of different modalities including, for example, MRI (e.g., functional MRI (fMRI)), positron emission tomography (PET), computed tomography (CT), electroencephalography (EEG), magnetoencephalography (MEG), and near-infrared spectroscopy (NIRS). In some embodiments, the multimodal neuroimaging data 424 includes anisotropic conductivity of brain tissue of the subject acquired using MM. In an embodiment, the multimodal neuroimaging data nay include combinations of data sets acquired using different modalities.

At block 508, the E-field simulation neural network 404 generates an estimation or prediction of electric fields that may be generated when the subject's brain is stimulated using the coil. As discussed above, the determination of the estimated electric fields may be based on the inputs including the detected coil position and orientation 420, the magnetic field profile 422 of the coil and the multimodal neuroimaging data 424 associated with the subject. In some embodiments, the E-field simulation neural network generates an estimated E-field for the whole brain of the subject. In some embodiments, the E-field simulation neural network 404 generates an estimated E-field for a selected region of the brain of the subject. At block 510, a graphical rendering module 406 is used to generate a graphical rendering of the simulated E-fields. The graphical rendering may be generated using rendering methods known in the art. In an embodiment, the E-field simulation neural network 404 and the graphical rendering module 406 may be implemented on a graphics processing unit (GPU) (e.g., GPU 808 shown in FIG. 8) of a computer system. At block 512, the graphical rendering may be provided to and displayed on a display 414. The graphical rendering may be stored in data storage (or memory) 412 of, for example, the E-field simulation and neuronavigation system (e.g., data storage 212 shown in FIG. 2) or other computer system.

Advantageously, the E-field simulation neural network 404 and graphics rendering module 406 may be used to visualize the electric field in real-time after an operator adjusts the position of the coil. Once the coil position and orientation are changed by an operator (and detected by the neuronavigation system 402), the E-field may also be adjusted in real-time to provide information about the actual brain site that is stimulated with the new coil position and orientation. In some embodiments, the E-field simulation neural network 204 may be configured to simulate the E-field (e.g., a whole brain E-field) within less than one second for a particular coil position and orientation.

Figure 6:
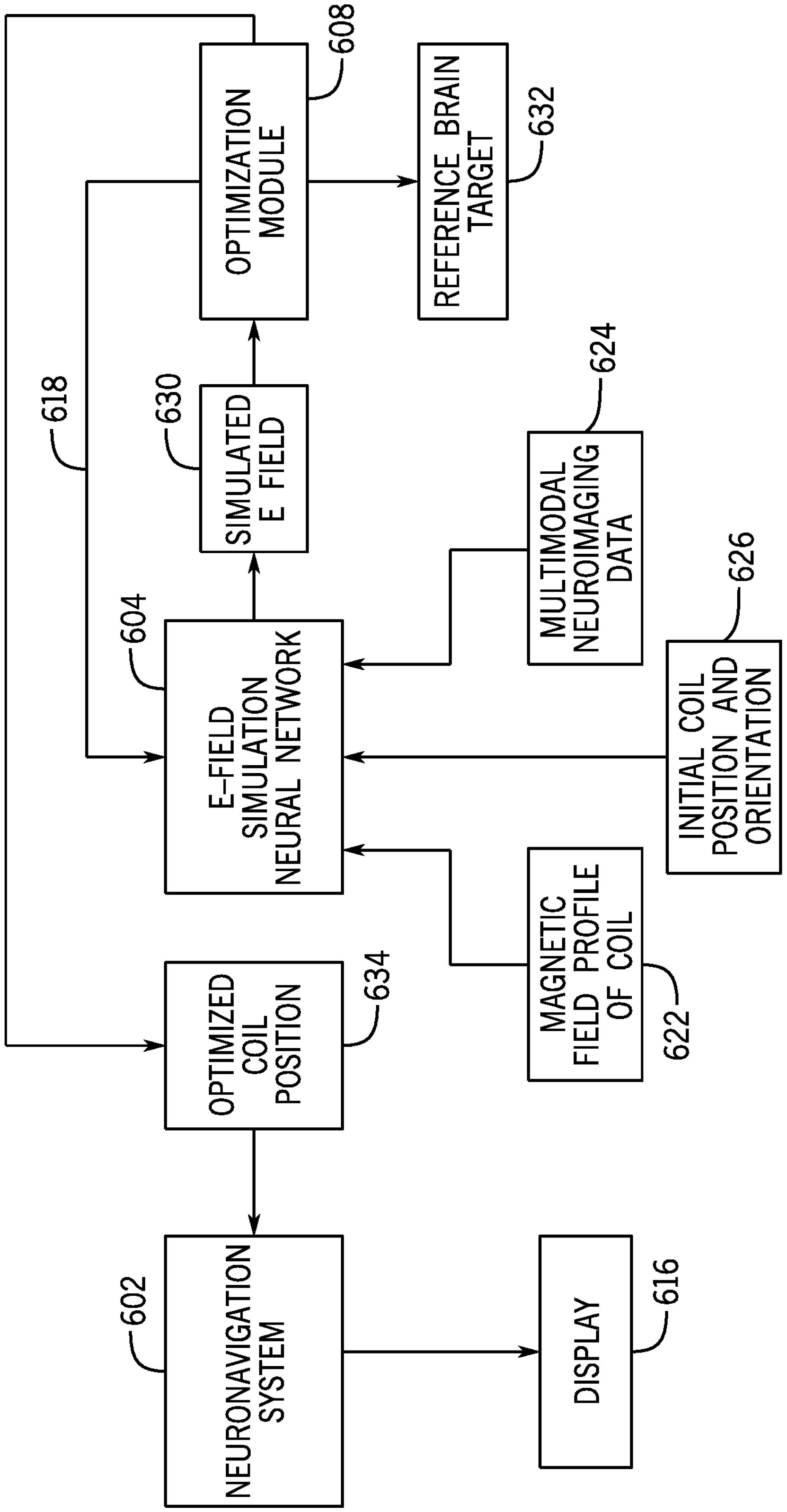
FIG. 6 is a block diagram of a workflow of the system of FIG. 2 for optimizing a magnetic coil position and orientation for neuromodulation in accordance with an embodiment.
Figure 7:
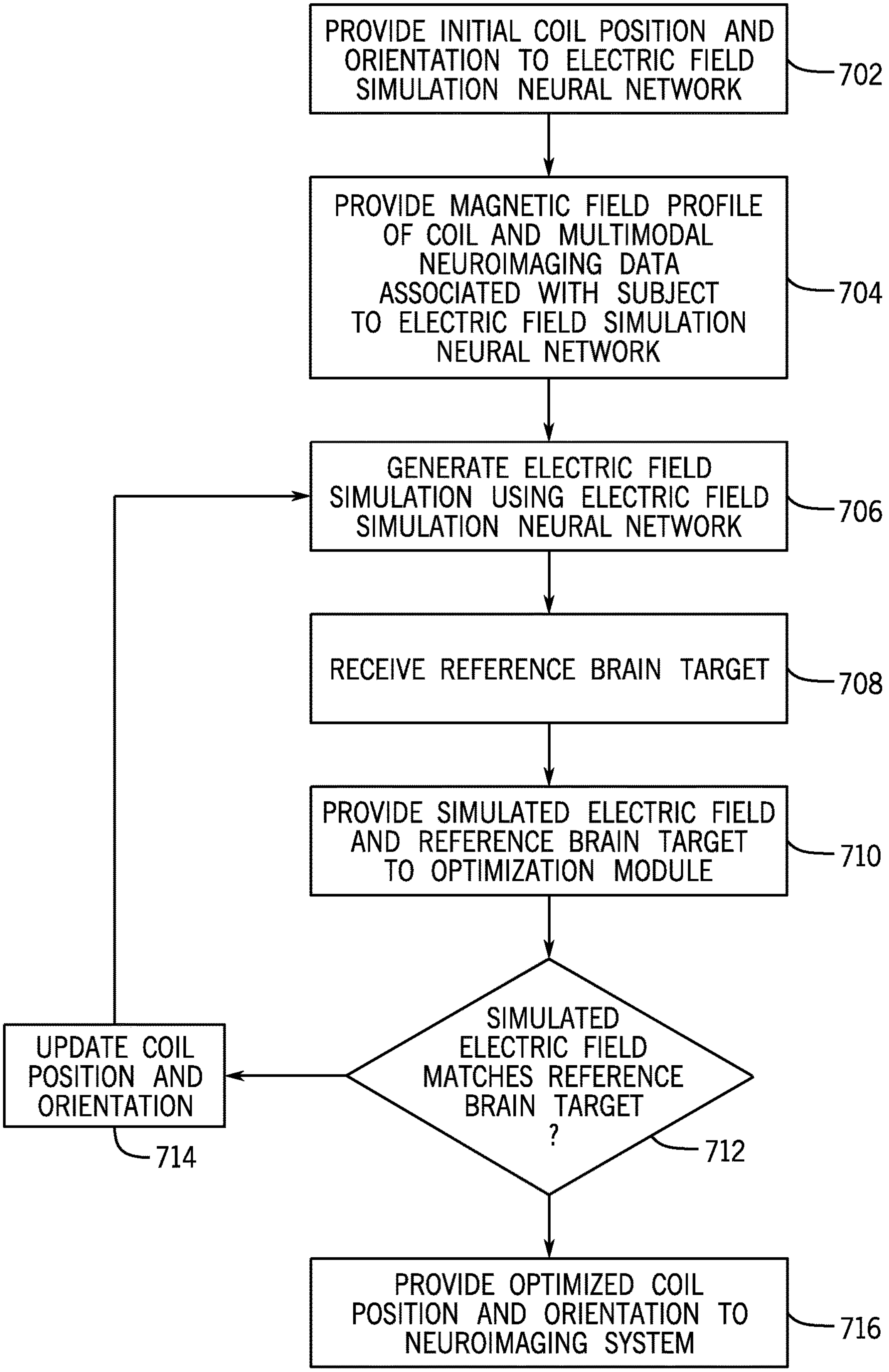
FIG. 7 illustrates a method for optimizing a magnetic coil position and orientation for neuromodulation in accordance with an embodiment.

As mentioned above with respect to FIG. 2, the system for integrated electric field simulation and neuronavigation may be configured to optimize a coil position and orientation for stimulation of a particular brain region. FIG. 6 is a block diagram of a workflow of the system of FIG. 2 for optimizing a magnetic coil position and orientation for neuromodulation in accordance with an embodiment and FIG. 7 illustrates a method for optimizing a magnetic coil position and orientation for neuromodulation in accordance with an embodiment. Referring to FIGS. 6 and 7, at block 702, an initial coil position and orientation 626 for a TMS coil (e.g., coil 108 shown in FIG. 1) may be provided to an E-field simulation neural network 604. In some embodiments, the initial coil position and orientation 626 may be provided by an operator using, for example, an input (e.g., input 210 shown in FIG. 2) or retrieved from a data storage (or memory) of, for example, the E-field simulation and neuronavigation system (e.g., data storage 212 shown in FIG. 2) or other computer system. In other embodiments, the initial coil position and orientation 626 may be provided by a neuronavigation system 602. At block 704, a magnetic field profile 622 of the TMS coil and multimodal neuroimaging data 624 associated with the subject are also provided as inputs to the E-field simulation neural network 604. In an embodiment, the magnetic field profile 622 of the coil and the multimodal neuroimaging data 624 associated with the subject may be retrieved from data storage (or memory) of, for example, the E-field simulation and neuronavigation system (e.g., data storage 212 shown in FIG. 2) or other computer system. Multimodal neuroimaging data 424 may be, for example, neuroimaging data of a subject's head and brain (e.g., functional and structural information) acquired using a plurality of different modalities including, for example, MRI (e.g., functional MRI (fMRI)), positron emission tomography (PET), computed tomography (CT), electroencephalography (EEG), magnetoencephalography (MEG), and near-infrared spectroscopy (NIRS). In some embodiments, the multimodal neuroimaging data 424 includes anisotropic conductivity of brain tissue of the subject acquired using MRI. In an embodiment, the multimodal neuroimaging data nay include combinations of data sets acquired using different modalities.

At block 706, the E-field simulation neural network 604 generates an estimation or prediction of electric fields (simulated E-fields 630) that may be generated when the subject's brain is stimulated using the coil. As discussed above, the determination of the estimated electric fields 630 may be based on the inputs including a coil position and orientation (e.g., the initial coil position and orientation 626 or an updated coil position and orientation as discussed further below), the magnetic field profile 622 of the coil and the multimodal neuroimaging data 624 associated with the subject. In some embodiments, the E-field simulation neural network 604 generates an estimated E-field for the whole brain of the subject. In some embodiments, the E-field simulation neural network generates an estimated E-field for a selected region of the brain of the subject. A block 708, a reference brain target 708 (e.g., an expected brain target for stimulation) is received, for example, the reference brain target may be provided as an input from an operator or the reference brain target may be retrieved from data storage. At block 710, the simulated E-field 630 and the reference brain target are provided to an optimization module 608. The optimization module 608 and E-field simulation neural network 604 may be configured to determine the optimal coil position and orientation to maximize the E-field at the reference brain target 632.

At block 712, the optimization module 608 may compare the simulated E-field 630 and the reference brain target 632 to determine if the simulated E-field for the coil position and orientation matches or corresponds to the reference brain target 632 and maximizes the E-field at the reference brain target 632. For example, the optimization module 608 may determine whether the estimated E-field from the simulated E-field 630 for a region that corresponds to the reference brain target 632 provided an E-field that is greater than a predetermined threshold value. If the simulated E-field for the initial coil position and orientation 626 does not match the reference brain target 632 at block 712, the optimization module 608 generates an updated coil position and orientation at block 714. The updated coil position and orientation may be provided to the E-field simulation neural network 604 via a feedback loop 618 and the process returns to block 706 and the E-field simulation neural network 604 generates a simulated E-field for the updated coil position and orientation. At block 712, if the simulated E-field for the initial 626 or updated coil position and orientation does match the reference brain target 632, at block 716 the optimized position and orientation 634 is provided to the neuronavigation system 602. The neuronavigation system 602 may display the optimized coil position and orientation on a display 616.

Accordingly, the system for integrated electric field simulation and neuronavigation can be configured to receive input from an operator of a TMS system about an expected brain target (e.g., the reference brain target 632) and automatically optimize the coil position and orientation so that the simulated electric field matches the brain target. Automatically optimizing the coil position to match the electric field with the expected brain target can improve the precision of brain stimulation. An operator can place the coil with the optimized position and orientation to precisely stimulate the expected brain target. In some embodiments, the optimization of a coil position and orientation for stimulation of a particular brain region using the system for integrated electric field simulation and neuronavigation may be used for treatment planning and can greatly improve the accuracy of diagnostic applications.

Figure 8:
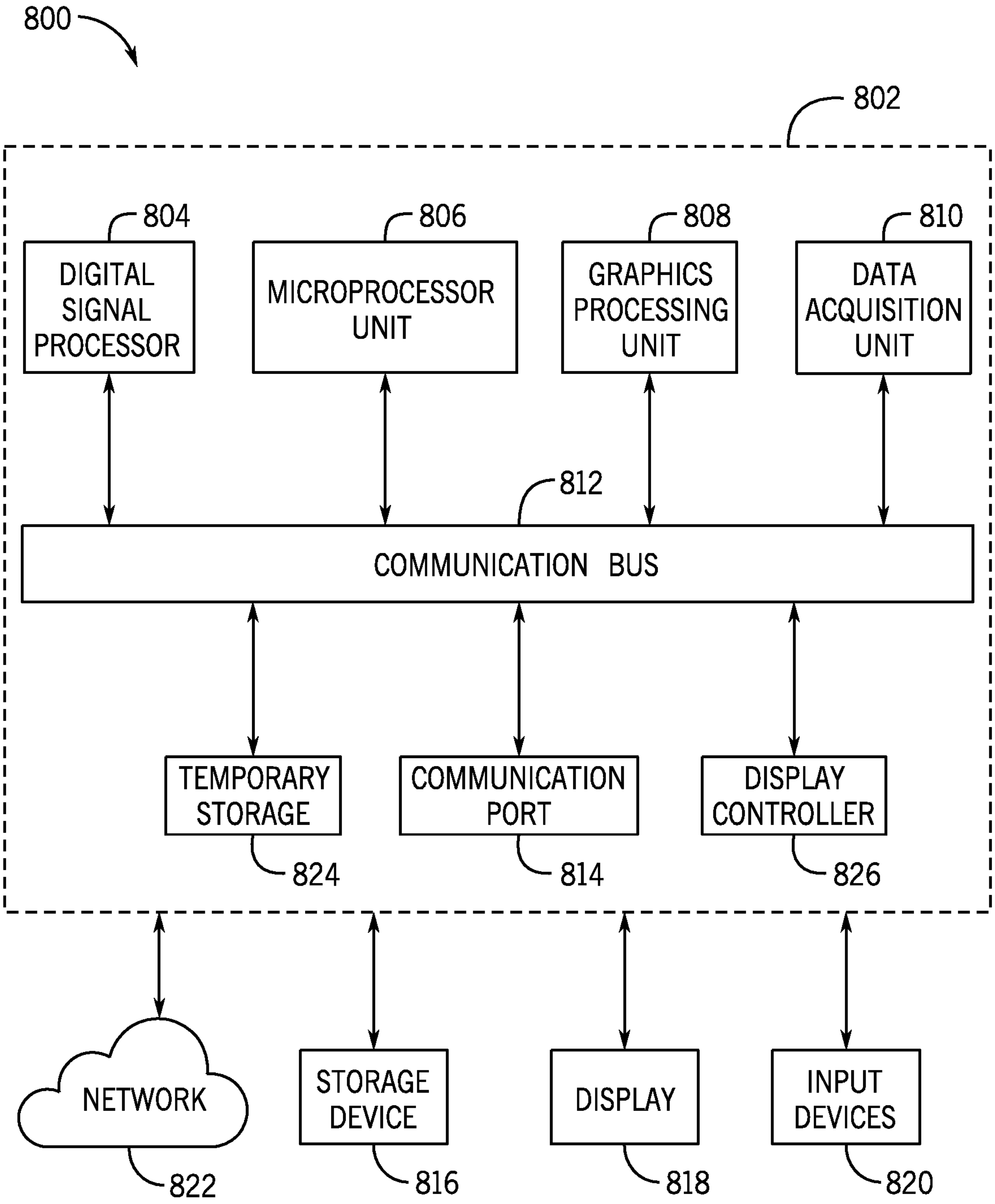
FIG. 8 is a block diagram of an example computer system in accordance with an embodiment.

FIG. 8 is a block diagram of an example computer system in accordance with an embodiment. Computer system 800 may be used to implement the systems and methods described herein. In some embodiments, the computer system 800 may be a workstation, a notebook computer, a tablet device, a mobile device, a multimedia device, a network server, a mainframe, one or more controllers, one or more microcontrollers, or any other general-purpose or application-specific computing device. The computer system 800 may operate autonomously or semi-autonomously, or may read executable software instructions from the memory or storage device 816 or a computer-readable medium (e.g., a hard drive, a CD-ROM, flash memory), or may receive instructions via the input device 822 from a user, or any other source logically connected to a computer or device, such as another networked computer or server. Thus, in some embodiments, the computer system 800 can also include any suitable device for reading computer-readable storage media.

Data, such as data acquired with an imaging system (e.g., a CT imaging system, a magnetic resonance imaging (MM) system, etc.) may be provided to the computer system 800 from a data storage device 816, and these data are received in a processing unit 802. In some embodiment, the processing unit 802 includes one or more processors. For example, the processing unit 802 may include one or more of a digital signal processor (DSP) 804, a microprocessor unit (MPU) 806, and a graphics processing unit (GPU) 808. The processing unit 802 also includes a data acquisition unit 810 that is configured to electronically receive data to be processed. The DSP 804, MPU 806, GPU 808, and data acquisition unit 810 are all coupled to a communication bus 812. The communication bus 812 may be, for example, a group of wires, or a hardware used for switching data between the peripherals or between any components in the processing unit 802.

The processing unit 802 may also include a communication port 814 in electronic communication with other devices, which may include a storage device 816, a display 818, and one or more input devices 820. Examples of an input device 820 include, but are not limited to, a keyboard, a mouse, and a touch screen through which a user can provide an input. The storage device 816 may be configured to store data, which may include data such as, for example, magnetic profiles of different types of electromagnetic coils, multimodal neuroimaging data, imaging data, etc., whether these data are provided to, or processed by, the processing unit 802. The display 818 may be used to display images and other information, such as magnetic resonance images, patient health data, and so on.

The processing unit 802 can also be in electronic communication with a network 822 to transmit and receive data and other information. The communication port 814 can also be coupled to the processing unit 802 through a switched central resource, for example the communication bus 812. The processing unit can also include temporary storage 824 and a display controller 826. The temporary storage 824 is configured to store temporary information. For example, the temporary storage 824 can be a random access memory.

Computer-executable instructions for integrated electric field simulation and neuronavigation, real-time graphical rendering of electric fields stimulated by an electromagnetic coil and optimization of coil position and orientation according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access The present invention has been described in terms of one or more preferred embodiments, and it should be appreciated that many equivalents, alternatives, variations, and modifications, aside from those expressly stated, are possible and within the scope of the invention.

The invention claimed is:

1. A system for integrated electric field simulation and neuronavigation, the system comprising;

a neuronavigation system configured to track an electromagnetic coil used for neuromodulation of a brain of a subject;

an electric field simulation neural network coupled to the neuronavigation system and configured to generate a simulated electric field for a region of interest based at least on a position and orientation of the electromagnetic coil, a magnetic field profile of the electromagnetic coil, and multimodal neuroimaging data associated with the subject; and a display coupled to the electric field simulation neural network and configured to display the simulated electric field.

2. The system according to claim 1, further comprising a processing unit of a computer system configured to perform as a graphical rendering module coupled to the electric field simulation neural network and configured to generate a graphical rendering of the simulated electric field.

3. The system according to claim 2, wherein the neuronavigation system is configured to detect the coil position and orientation and to provide the coil position and orientation to the electric field simulation neural network.

4. The system according to claim 2, wherein the display is configured to display the graphical rendering of the simulated electric field.

5. The system according to claim 1, further comprising a processing unit of a computer system configured to perform as an optimization module coupled to the electric field simulation neural network, wherein the optimization module and the electric field simulation neural network are configured to determine an optimized coil position and orientation for a brain target.

6. The system according to claim 5, wherein the optimized coil position and orientation is provided to the neuronavigation system.

7. The system according to claim 1, wherein the region of interest is the brain of the subject.

8. The system according to claim 1, wherein the region of interest is a region of the brain of the subject.

9. The system according to claim 1, wherein the electric field simulation neural network is a convolutional neural network.

10. The system according to claim 1, wherein the electric field simulation neural network is configured to generate the simulated electric field in less than one second.

11. The system according to claim 1, wherein the multimodal neuroimaging data includes neuroimaging data of the head and brain of the subject acquired using a plurality of different modalities.

12. The system according to claim 1, wherein the multimodal neuroimaging data includes anisotropic conductivity of brain tissue of the subject.

13. The system according to claim 1, wherein the electromagnetic coil is a transcranial magnetic stimulation (TMS) coil.

14. A method for generating a graphical rendering of a simulated electric field using a system for integrated electric field simulation and neuronavigation, the method comprising:

detecting, using a neuronavigation system, a position and orientation of an electromagnetic coil used for neuromodulation of a brain of a subject;

providing the position and orientation of the electromagnetic coil, a magnetic field profile of the electromagnetic coil and multimodal neuroimaging data associated with the subject to an electric field simulation neural network;

generating, using the electric field simulation neural network, a simulated electric field for a region of interest based at least on the position and orientation of the electromagnetic coil, the magnetic field profile of the electromagnetic coil, and the multimodal neuroimaging data associated with the subject;

generating, using a processing unit of a computer system configured to perform as a graphical rendering module, a graphical rendering of the simulated electric field; and displaying the graphical rendering on a display.

15. The method according to claim 14, wherein the region of interest is the brain of the subject.

16. The method according to claim 14, wherein the electromagnetic coil is a transcranial magnetic stimulation (TMS) coil.

17. The method according to claim 14, wherein the electric field simulation neural network is a convolutional neural network.

18. A method for using a system for integrated electric field simulation and neuronavigation, the method comprising:

providing a position and orientation of an electromagnetic coil, a magnetic field profile of the electromagnetic coil, and multimodal neuroimaging data associated with a subject to an electric field simulation neural network, wherein the electromagnetic coil is used for neuromodulation of a brain of the subject;

generating, using the electric field simulation neural network, a simulated electric field for a region of interest based at least on the position and orientation of the electromagnetic coil, the magnetic field profile of the electromagnetic coil, and the multimodal neuroimaging data associated with the subject;

receiving a reference target in the region of interest;

comparing, using a processing unit of a computer system configured to perform as an optimization module, the simulated electric field to the reference target to determine if the position and orientation of the electromagnetic coil maximizes an electric field at the reference target in the region of interest; and providing the position and orientation of the electromagnetic coil to a neuronavigation system if the position and orientation of the electromagnetic coil maximizes an electric field at the reference target in the region of interest.

19. The method according to claim 18, wherein the region of interest is the brain of the subject.

20. The method according to claim 18, wherein the electric field simulation neural network is a convolutional neural network.

21. The method according to claim 18, wherein the electromagnetic coil is a transcranial magnetic stimulation (TMS) coil.

* * * * *